United States Patent [19]

Bundy et al.

[11] 4,152,523

[45] May 1, 1979

[54] 11-DEOXY-17-PHENYL-13,14-DIHYDRO-PGE$_1$ COMPOUNDS

[75] Inventors: Gordon L. Bundy, Kalamazoo; Norman A. Nelson, Galesburg, both of Mich.

[73] Assignee: The Upjohn Company, Kalamazoo, Mich.

[21] Appl. No.: 772,830

[22] Filed: Feb. 28, 1977

Related U.S. Application Data

[62] Division of Ser. No. 542,372, Jan. 20, 1975, Pat. No. 4,029,693.

[51] Int. Cl.$^2$ .......................................... C07C 177/00
[52] U.S. Cl. ...................................... 560/53; 562/463
[58] Field of Search .......................... 560/53; 562/463

[56] References Cited

U.S. PATENT DOCUMENTS

3,971,826  7/1976  Hess et al. ..................... 260/520 B

FOREIGN PATENT DOCUMENTS

7301094  7/1973  Netherlands ............................ 260/473

*Primary Examiner*—Paul J. Killos
*Attorney, Agent, or Firm*—Robert A. Armitage

[57] ABSTRACT

This invention comprises 11-deoxy-17-phenyl-18,19,20-trinor-prostaglandin-type compounds which exhibit prostaglandin-type pharmacological activity, such as lowering blood pressure, inhibiting gastric secretion, regulating the reproductive cycle, and the like.

22 Claims, No Drawings

11-DEOXY-17-PHENYL-13,14-DIHYDRO-PGE$_1$ COMPOUNDS

The present application is a divisional application of Ser. No. 542,372, filed Jan. 20, 1975, now issued as U.S. Pat. No. 4,029,693, on June 14, 1977.

The present invention relates to prostaglandin analogs for which the essential material constituting a disclosure therefor is incorporated by reference here from U.S. Pat. No. 4,029,693, issued June 14, 1977.

We claim:

1. A compound of the formula

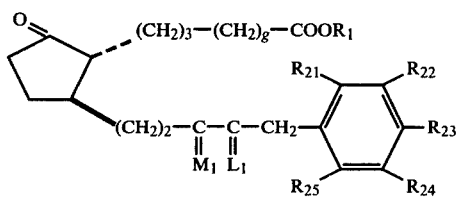

or a mixture comprising that compound and the enantiomer thereof;
wherein g is 3 to 5, inclusive;
wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one or two alkyl of one to 3 carbon atoms, inclusive, or chloro, or a pharmacologically acceptable cation;
wherein L$_1$ is

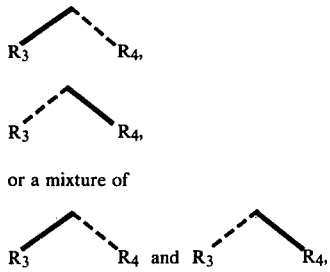

or a mixture of

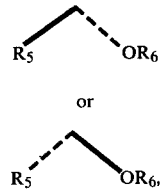

wherein R$_3$ and R$_4$ are hydrogen or methyl, being the same or different;
wherein M$_1$ is

or

wherein R$_5$ and R$_6$ are hydrogen or methyl, with the proviso that R$_5$ is methyl only when R$_6$ is hydrogen and R$_6$ is methyl only when R$_5$ is hydrogen;
wherein R$_{21}$, R$_{22}$, R$_{23}$, R$_{24}$, and R$_{25}$ are hydrogen, fluoro, chloro, trifluoromethyl, alkyl of one to 4 carbon atoms, inclusive, or —OR$_8$ wherein R$_8$ is alkyl of one to 3 carbon atoms, inclusive, with the proviso that at least two of R$_{21}$, R$_{22}$, R$_{23}$, R$_{24}$, and R$_{25}$ are hydrogen, and not more than two of R$_{21}$, R$_{22}$, R$_{23}$, R$_{24}$, and R$_{25}$ are chloro, fluoro, trifluoromethyl or —OR$_8$.

2. A compound according to claim 1, wherein M$_1$ is

3. A compound according to claim 2, wherein g is 5.
4. A compound according to claim 3, wherein R$_{21}$, R$_{22}$, R$_{23}$, R$_{24}$, and R$_{25}$ are hydrogen, or four of R$_{21}$, R$_{22}$, R$_{23}$, R$_{24}$, and R$_{25}$ are hydrogen and one of R$_{21}$, R$_{22}$, R$_{23}$, R$_{24}$, and R$_{25}$ is chloro, fluoro, or trifluoromethyl.
5. A compound according to claim 4, wherein M$_1$ is

H / OH.

6. A compound according to claim 5, wherein L$_1$ is

H / H.

7. A compound according to claim 6, wherein R$_1$ is hydrogen, alkyl of one to 4 carbon atoms, inclusive, or a pharmacologically cation.
8. 2a,2b-Dihomo-11-deoxy-17-(m-chlorophenyl)-18,19,20-trinor-13,14-dihydro-PGE$_1$, methyl ester, a compound according to claim 7.
9. 2a,2b-Dihomo-11-deoxy-17-phenyl-18,19,20-trinor-13,14-dihydro-PGE$_1$, methyl ester, a compound according to claim 7.
10. 2a,2b-Dihomo-11-deoxy-17-(m-trifluoromethylphenyl)-18,19,20-trinor-13,14-dihydro-PGE$_1$, methyl ester, a compound according to claim 7.
11. A compound according to claim 2, wherein g is 3.
12. A compound according to claim 11, wherein R$_{21}$, R$_{22}$, R$_{23}$, R$_{24}$, and R$_{25}$ are hydrogen or four of R$_{21}$, R$_{22}$, R$_{23}$, R$_{24}$, and R$_{25}$ are hydrogen and one of R$_{21}$, R$_{22}$, R$_{23}$, R$_{24}$ and R$_{25}$ is chloro, fluoro, or trifluoromethyl.
13. A compound according to claim 12, wherein R$_5$ is methyl.
14. A compound according to claim 12, wherein R$_6$ is methyl.
15. A compound according to claim 12, wherein R$_5$ and R$_6$ are hydrogen.
16. A compound according to claim 15, wherein R$_3$ is methyl and R$_4$ is hydrogen.
17. A compound according to claim 15, wherein R$_3$ and R$_4$ are both methyl.
18. A compound according to claim 15, wherein R$_3$ and R$_4$ are hydrogen.
19. 11-Deoxy-17-(m-chlorophenyl)-18,19,20-trinor-13,14-dihydro-PGE$_1$, a compound according to claim 18.
20. 11-Deoxy-17-phenyl-18,19,20-trinor-13,14-dihydro-PGE$_1$, a compound according to claim 18.
21. 11-Deoxy-17-(m-trifluoromethylphenyl)-18,19,20-trinor-13,14-dihydro-PGE$_1$, a compound according to claim 18.
22. A compound according to claim 1, wherein M$_5$ is

* * * * *